US010143480B2

(12) United States Patent
Victor et al.

(10) Patent No.: US 10,143,480 B2
(45) Date of Patent: Dec. 4, 2018

(54) DISPOSABLE CUTTER ACETABULAR REAMER

(71) Applicant: Greatbatch Ltd., Clarence, NY (US)

(72) Inventors: Gary C. Victor, Wheatfield, NY (US); Sean P. Curry, Chatham, NJ (US); Steven W. Winn, Lancaster, NY (US)

(73) Assignee: Viant AS&O Holdings, LLC, Tempe, AZ (US)

( * ) Notice: Subject to any disclaimer, the term of this patent is extended or adjusted under 35 U.S.C. 154(b) by 490 days.

(21) Appl. No.: 14/746,386

(22) Filed: Jun. 22, 2015

(65) Prior Publication Data

US 2015/0366568 A1    Dec. 24, 2015

Related U.S. Application Data

(60) Provisional application No. 62/014,914, filed on Jun. 20, 2014.

(51) Int. Cl.
*A61B 17/16*    (2006.01)
(52) U.S. Cl.
CPC ........ *A61B 17/1666* (2013.01); *A61B 17/162* (2013.01); *A61B 17/1615* (2013.01); *A61B 17/1659* (2013.01)
(58) Field of Classification Search
CPC ................................. A61B 17/1666
See application file for complete search history.

(56) References Cited

U.S. PATENT DOCUMENTS

| 5,295,992 | A | 3/1994 | Cameron |
| 6,890,336 | B2 | 5/2005 | Nordman et al. |
| 8,357,163 | B2 | 1/2013 | Sidebotham et al. |
| 8,454,608 | B2 | 6/2013 | White et al. |
| 8,518,043 | B2 | 8/2013 | Sidebotham et al. |
| 8,535,316 | B2 | 9/2013 | Lewis et al. |
| 8,556,897 | B2 | 10/2013 | Sidebotham et al. |
| 8,679,124 | B2 | 3/2014 | Lechot et al. |
| 2009/0163921 | A1* | 6/2009 | Lechot ............... A61B 17/1617 606/81 |

(Continued)

OTHER PUBLICATIONS

EPSearch Application 15173133.8 dated Oct. 27, 2015.
Extended European Search Report, Application No. 15173133.8, dated Oct. 27, 2015.

*Primary Examiner* — Marcia Watkins
(74) *Attorney, Agent, or Firm* — Grossman, Tucker, Perreault & Pfleger, PLLC

(57) ABSTRACT

An orthopedic bone cutter for cutting bone and tissue is described. The cutting device comprises a support frame having a plurality of radially extending struts to which a cutting shell is removably connected thereto. The frame serves as a universal support structure that provides added mechanical support and stability to which various embodiments of cutting shells may be connected thereto. The bone cutter of the present invention is designed such that the cutting shell may comprise a variety of embodiments that enable the removal of bone and tissue. Embodiments of the cutting shell may comprise at least a partially hemispherical shape in which a plurality of cutting surfaces may extend. In addition, the cutting shell may comprise a plurality of removal cutting blade inserts that are received within slots that extend through the shell thickness.

28 Claims, 14 Drawing Sheets

(56) References Cited

U.S. PATENT DOCUMENTS

| | | |
|---|---|---|
| 2011/0202060 A1* | 8/2011 | White ................ A61B 17/1666 606/80 |
| 2012/0191099 A1 | 7/2012 | Victor et al. |
| 2013/0204254 A1 | 8/2013 | Slone et al. |
| 2013/0245628 A1* | 9/2013 | Sidebotham ........... A61B 17/16 606/80 |
| 2014/0025078 A1 | 1/2014 | Sidebotham et al. |
| 2014/0107651 A1 | 4/2014 | Meridew et al. |

\* cited by examiner

DISPOSABLE CUTTER ACETABULAR REAMER

CROSS REFERENCE TO RELATED APPLICATION

This application claims priority from U.S. Provisional Application Ser. No. 62/014,914, filed Jun. 20, 2014.

TECHNICAL FIELD

This invention relates to the art of instruments used in orthopedic surgery. More specifically, this invention relates to an acetabular reamer for cutting the cotyloid cavity of the acetabulum for the placement of a hip joint prosthetic cup.

BACKGROUND OF THE INVENTION

Bone cutters, such as acetabular reamers, are surgical tools which are used to cut a partial hemispherically-shaped cavity within a bone. In particular, an acetabular reamer is an orthopedic surgical tool used to cut a partial hemispherically-shaped cavity within a pelvic bone for the insertion of a prosthetic cup during an artificial hip joint procedure.

Acetabular reamers must be capable of producing cavities having precise dimensions to ensure the proper positioning of a prosthetic cup within the pelvic bone. As such, traditional reamers, such as those disclosed in U.S. Pat. No. 4,811,632 to Salyer, are constructed having a hemispherical cup-like shape. These prior art reamers are fabricated with a plurality of cutting surfaces that are precisely positioned extending from the curved surface of the curved reamer shell. The hemispherical cup-like body construction provides the reamer with structural rigidity that enables a precise cut. Fabrication of these traditional reamers is often difficult and cost prohibitive. Traditional reamers like that of Salyer require precise positioning of a multitude of cutting surfaces along a curved convex shape of a reamer shell. This requires the use of intricate tooling and expertise. Therefore, because of the high cost of these tools, traditional reamers are often cleaned and sterilized for reuse in multiple surgical procedures.

However, traditional reamers, like Salyer, are often difficult to clean and sterilize. After use, soft tissue embedded in the tool is often difficult to remove. As a result, the surfaces of these reamers may become contaminated with bacteria or micro-organisms which may cause adverse surgical outcomes. Consequently, cutting tools, such as those disclosed by Stamp in U.S. patent application Pub. No. 2013/0267957, that are intended for single use have been developed. After such use, the cutting tool is simply discarded.

Single use cutting tools, however, typically lack structural rigidity which may adversely affect patient outcomes. Such structural rigidity minimizes unintended deflection of the cutting edge of the cutting tool that might result in an undesirable patient outcome. Deflection of a portion of the cutting tool, in particular deflection of a cutting edge against the surface of a bone during use could result in an inaccurate cut or deformed bone surface that is not desired. The cutting tool of Stamp, for example, requires the use of an additional support substrate that is used to structurally reinforce the cutting tool and minimize blade deflection.

The bone cutter of the present invention, unlike Stamp, is specifically designed to increase structural rigidity while minimizing the amount of material needed to construct the tool. Thus, improved rigidity while minimizing the amount of material used to construct the reamer provides a cutting tool that is more accurate during use; the unique structural design of the present cutting tool minimizes structural distortion under a mechanical load. Furthermore, by minimizing the amount of material required to construct the tool, the bone cutter of the present invention is more cost effective and easier to manufacture.

Therefore, what is needed is a low cost bone cutter that is easier to manufacture while providing improved structural rigidity.

Still further, what is needed is a method of manufacturing a cost effective bone cutter that provides at least a partial hemispherical form and where the cutter is not as susceptible to mechanical deflection as reamers of the prior art to consequently ensure accurate cutting.

SUMMARY OF THE INVENTION

A bone cutter designed to form at least a partial hemispherically shaped concave cavity in a bone, particularly for use to facilitate the implantation of a prosthetic cup during a hip replacement surgical procedure, is provided. The bone cutter of the present invention comprises a reamer shell having a structure that is at least partially hemispherical and a support frame having a plurality of spaced apart struts that longitudinally extend from a frame base. The support frame of the present invention is designed to provide structural support to the bone cutter. In addition, the frame is designed to be removably positioned within an interior of the reamer shell, thus providing structural support to a cutting shell of a variety of shapes and sizes.

In a preferred embodiment, the support frame is of a universal design that can be easily attached and removed from the bone cutting shell, thereby enabling a physician to easily change the cutting surface. For example, the bone cutting shell is preferably replaced before each surgical procedure to ensure sharp, sterile cutting blades. Alternatively, the cutting shell can be easily replaced during a surgical procedure if the cutting surface is discovered to be dull.

As will be discussed in more detail, various embodiments of attachment mechanisms may be used to connect the cutting shell to the frame are disclosed. In one embodiment, a fastener such as a rivet or screw may be used to connect the shell to the frame. In another embodiment, a tongue and groove mechanism may be used to removably connect the frame to the shell.

The support frame is of a universal design that can be used to support a variety of cutting shells of various shapes and sizes. In particular, the cutting shell may comprise at least a partially hemispherical shell having a plurality of cutting teeth that extend from an exterior surface of the shell. In an alternative embodiment, the shell may comprise a plurality of cutting blade inserts that are removably positioned within the thickness of the sidewall of the shell. Still yet a third embodiment is of a hemispherically shaped shell that comprises a plurality of spaced apart longitudinal and lateral positioned ribs. A cutting blade preferably extends outwardly from an exterior surface of at least a portion of the ribs.

BRIEF DESCRIPTION OF THE DRAWINGS

FIG. 2A illustrates a magnified cross-sectional view of an embodiment of the base of the support frame comprising a ledge portion.

DETAILED DESCRIPTION OF THE PREFERRED EMBODIMENT

Figure 1:
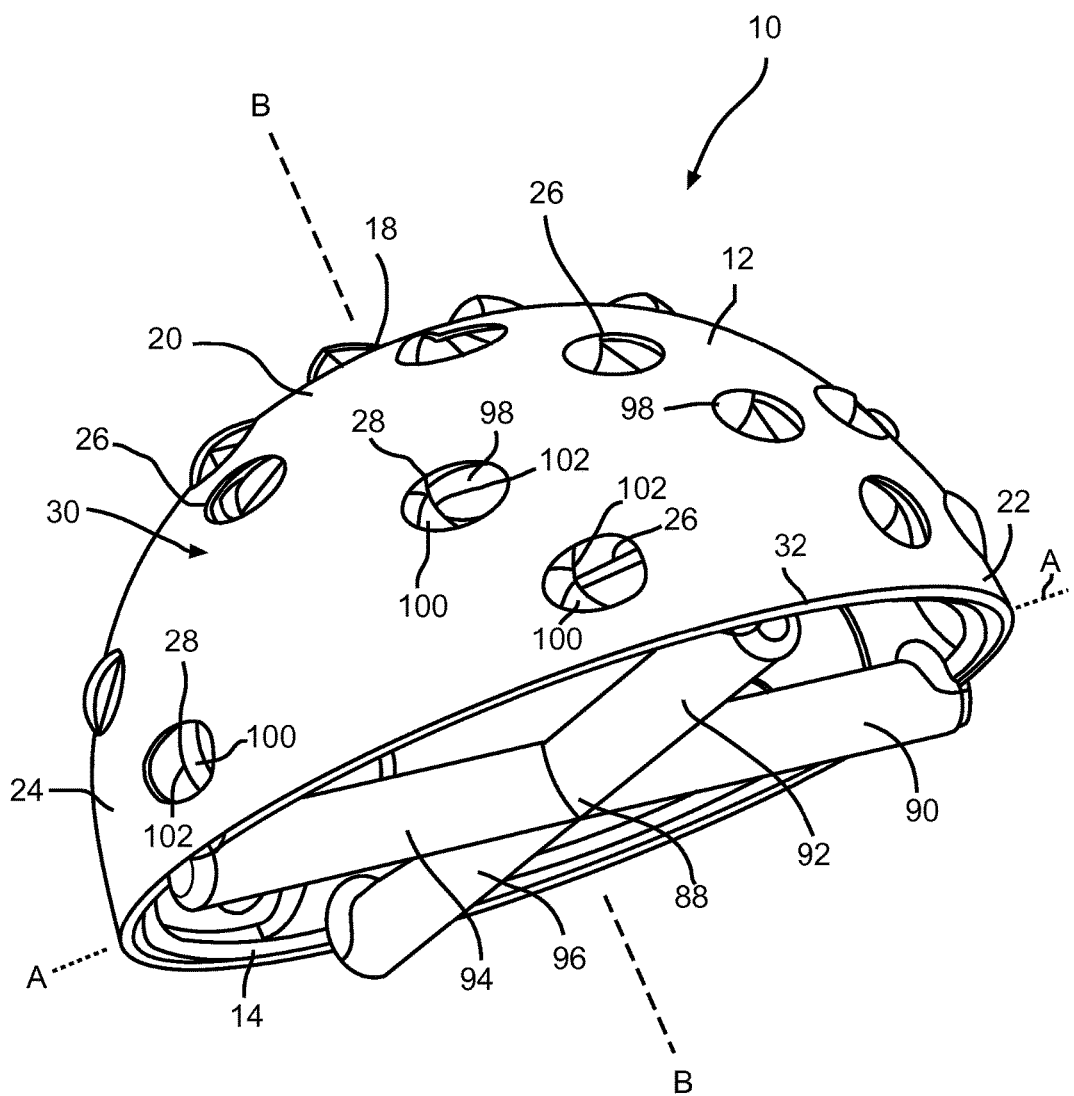
FIG. 1 illustrates an embodiment of the bone cutter of the present invention.
Figure 2:
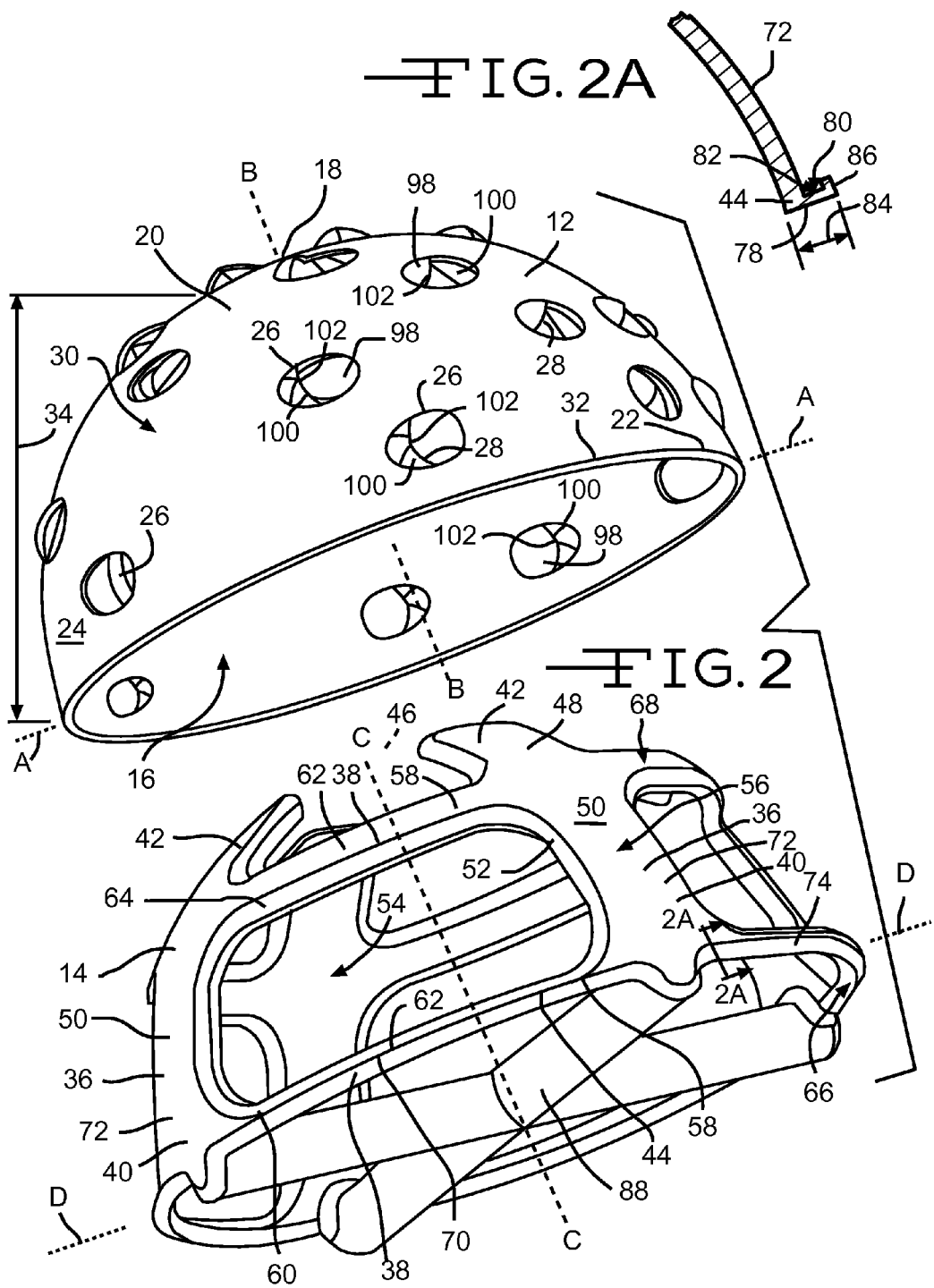
FIG. 2 shows an embodiment of a cutting shell and a support frame that comprise the bone cutter of the present invention.
Figure 3:
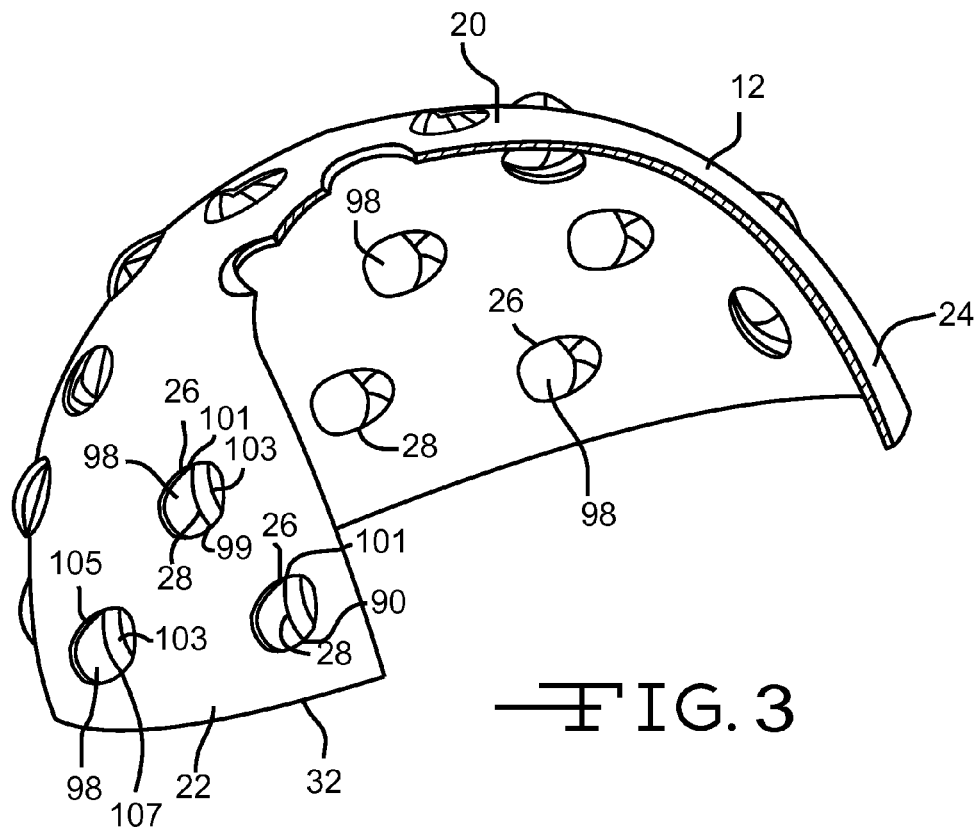
FIG. 3 illustrates a partially broken perspective view of the cutting shell embodiment shown in FIG. 2.
Figure 4:
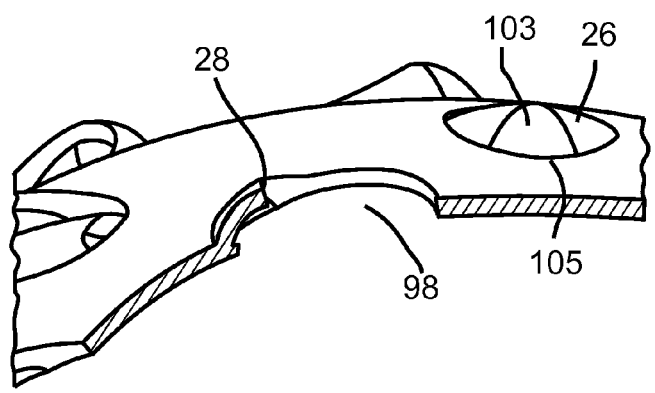
FIG. 4 shows a magnified cross-sectional view of the cutting shell shown in FIG. 2.

Now turning to the figures, FIGS. 1 and 2 illustrate a preferred embodiment of a bone cutter 10 of the present invention. As illustrated, the bone cutter 10 preferably comprises a cutting shell 12 that is removably connectable to a support frame 14. In a preferred embodiment, the support frame 14 is positioned within an interior 16 of the cutting shell 12 to provide mechanical and structural support to the bone cutter 10. The support frame 14 is preferably of a universal design that is intended to be utilized with a plurality of cutting shells having a variety of shapes and sizes. The support frame 14 is designed to be easily removed from the cutting shell 12 and subsequently re-inserted within a new cutting shell 12.

The cutting shell 12 is preferably of at least a partially hemispherical shape. As illustrated, the cutting shell 12 comprises a shell apex 18 located at a bone cutter distal end 20 that extends from a bone cutter base 22 located at an imaginary equatorial base plane A-A (FIG. 2) at a bone cutter proximal end 24. The cutting shell 12 comprises a plurality of cutting teeth 26, each having a cutting surface 28 that is raised from an exterior surface 30 of the cutting shell 12. A rotational axis B-B extends through the apex 18.

In a preferred embodiment, the bone cutter base 22 defines an annular bone cutter outer perimeter at a lower base edge 32 of the cutter 10 having a diameter ranging from about 20 mm to about 80 mm. The bone cutter 10 also has a height 34 that extends from the lower base edge 32 to the apex 18 (FIG. 2). It is preferred that the bone cutter height 34 may range from about 10 mm to about 50 mm.

Figure 8:
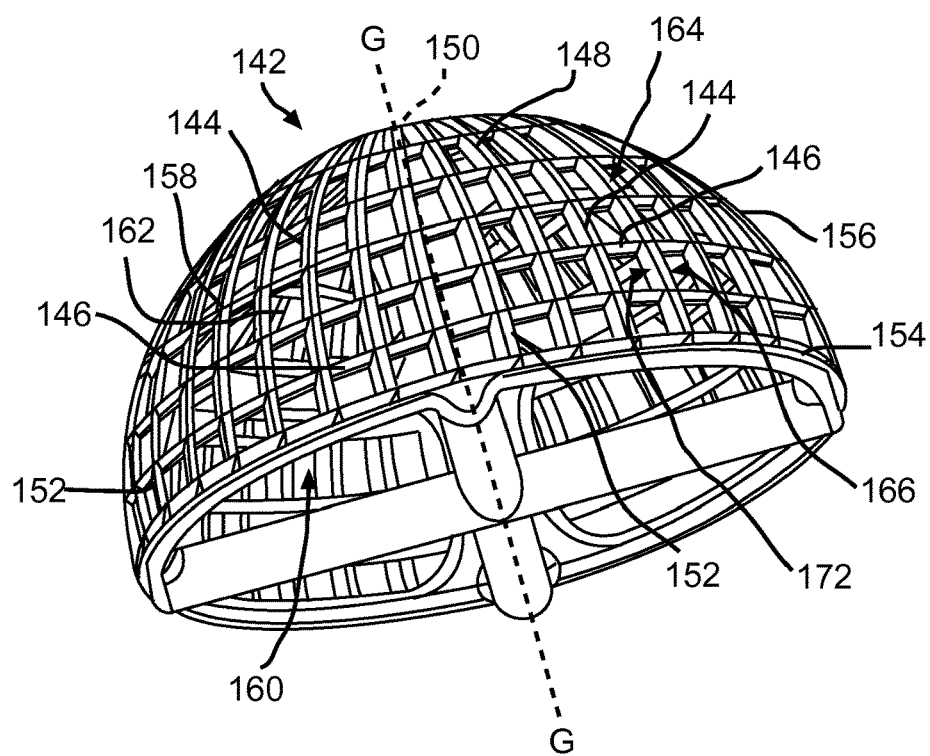
FIG. 8 illustrates an alternative embodiment of a cutting shell comprising a plurality of first and second longitudinally and laterally extending ribs that utilizes the support frame of the present invention.
Figure 15:
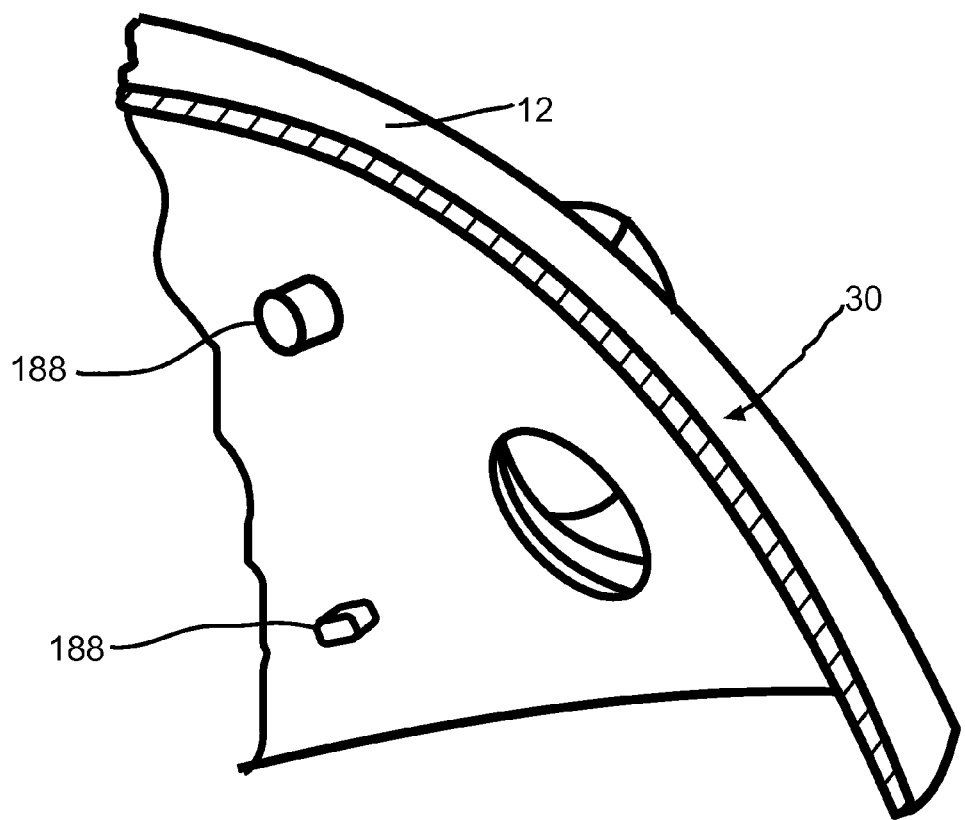
FIG. 15 shows an embodiment of an attachment mechanism in which various tongue members may extend from an interior surface of a cutting shell.

FIGS. 2, 8 and 15 illustrate an embodiment of the support frame 14. As shown, the support frame 14 comprises a plurality of spaced apart longitudinally extending first struts 36 and laterally extending second struts 38 that together form at least a partial hemispherical shape. In a preferred embodiment, each of the plurality of first struts 36 comprises an elongated length having a curved shape that extends longitudinally along the rotational axis C-C from a strut proximal end 40 to a strut distal end 42. As illustrated, each of the first strut proximal ends 40 extend radially and outwardly from a frame base 44 while the first strut distal ends 42 extend inwardly toward rotational axis C-C and imaginary frame apex 46 located at a frame distal end 48.

In addition, each of the first struts 36 preferably comprises a first strut sidewall 50 having a first strut thickness 52 with opposing interior and exterior sidewall surfaces 54, 56 that extend perpendicular to the first strut length (FIG. 2). In a preferred embodiment, each of the first strut sidewalls 50 has a convexo-concave shape with the exterior surface 56 comprising an outwardly extending convex shape and the interior surface 54 having an inwardly extending concave shape with respect to rotational axis C-C.

The plurality of spaced apart second struts 38 are positioned laterally between adjacent longitudinally extending first struts 36. Similar to the first struts 36, each of the second struts 38 comprises an elongated length having a curved shape that extends laterally between adjacent first struts 36 from a second strut proximal end 58 to a second strut distal end 60. Each of the second struts 38 preferably comprises a second strut sidewall 62 having a second strut thickness 64 with opposing interior and exterior sidewall surfaces 66, 68. As illustrated, similar to the first struts 36, each of the second strut sidewalls 62 has a convexo-concave shape with the second strut sidewall exterior surface 68 having an outwardly extending convex shape and the second sidewall interior surface 66 having an inwardly extending concave shape with respect to the rotational axis C-C.

In the embodiment shown in FIG. 2, the frame 14 comprises four first struts 36 that extend longitudinally from the frame base 44. In addition, a total of eight second struts 38 are positioned between adjacent first struts 36. As illustrated, four second struts 38 are positioned about the frame distal end 48, each of them extending between longitudinally positioned first struts 36. In addition, four second struts 38 are positioned at the frame base 44 between adjacent first struts 36. The plurality of the second struts 38 positioned at the frame base 44 preferably forms an annular frame base end 70 having a frame base perimeter located at an imaginary equatorial frame base plane D-D (FIG. 2) at a support frame proximal end 72. It is contemplated however, that an additional or a fewer number of first or second struts 36, 38 may be utilized to form the bone cutter support frame 14.

In a preferred embodiment, the support frame base perimeter 74 is less than the cutting shell base perimeter. This is to ensure that the support frame 14 is positionable within the interior 16 of the cutting shell 12. In a preferred embodiment when the support frame 14 is positioned within the interior 16 of the cutting shell 12, the imaginary equatorial base planes A-A, D-D of the respective cutting shell 12 and support frame 14 are about coplanar. Alternatively, the support frame equatorial base plane D-D may be positioned above, or proximal, of the cutting shell equatorial base plane A-A. This alternative position of the support frame 14 within the interior 16 of the cutting shell 12 thus minimizes possible contact of the support frame 14 with surrounding bone and tissue during a surgical procedure. Furthermore, this preferred position of the support frame 14 within the cutting shell interior 16 enables improved articulation of a connected drive shaft 76 (FIG. 17).

As illustrated in FIGS. 2 and 2A, the base 44 of the support frame 14 may comprise a ledge 78 that extends outwardly from the frame proximal end 72. In addition, the ledge 78 preferably comprises a ledge shelf 80 that extends annularly about the frame base 44. The ledge shelf 80 has a surface 82 that extends outwardly from the base perimeter of the frame 14. In a preferred embodiment, the ledge shelf surface 82 extends about perpendicular to the rotating axis C-C at the frame base 70 such that the ledge surface 82 and the imaginary equatorial frame base plane C-C are about co-planar. The ledge 82 provides a surface on which the shell thickness at the cutting shell base end 22 may be positioned. The ledge shelf 80 preferably has a width 84 that is dimensioned about the same as the shell sidewall thickness at the cutting shell base end 22. The frame ledge 80 may also comprise a ledge lip 86 that extends upwardly towards the frame distal end 48. The ledge lip 86 provides added mechanical stability and support of the cutting shell 12 when attached to the frame 14.

The support frame 14 may be composed of a polymeric material. Examples of polymeric materials include, but are not limited to, acrylonitrile butadiene styrene, an acrylic polymer, nylon, or polyethylene. In addition, the frame 14 may also be constructed of a metallic material. Examples of metallic materials may include but are not limited to, stainless steel, aluminum, titanium, MP35N, cobalt chromium alloys, and titanium aluminum alloys. Furthermore, the support frame 14 may be composed of a ceramic material such as alumina, boron nitride, or aluminum nitride. It is contemplated that the support frame 14 of the present invention may comprise a combination of different polymeric, metallic and/or ceramic materials.

Figure 17:
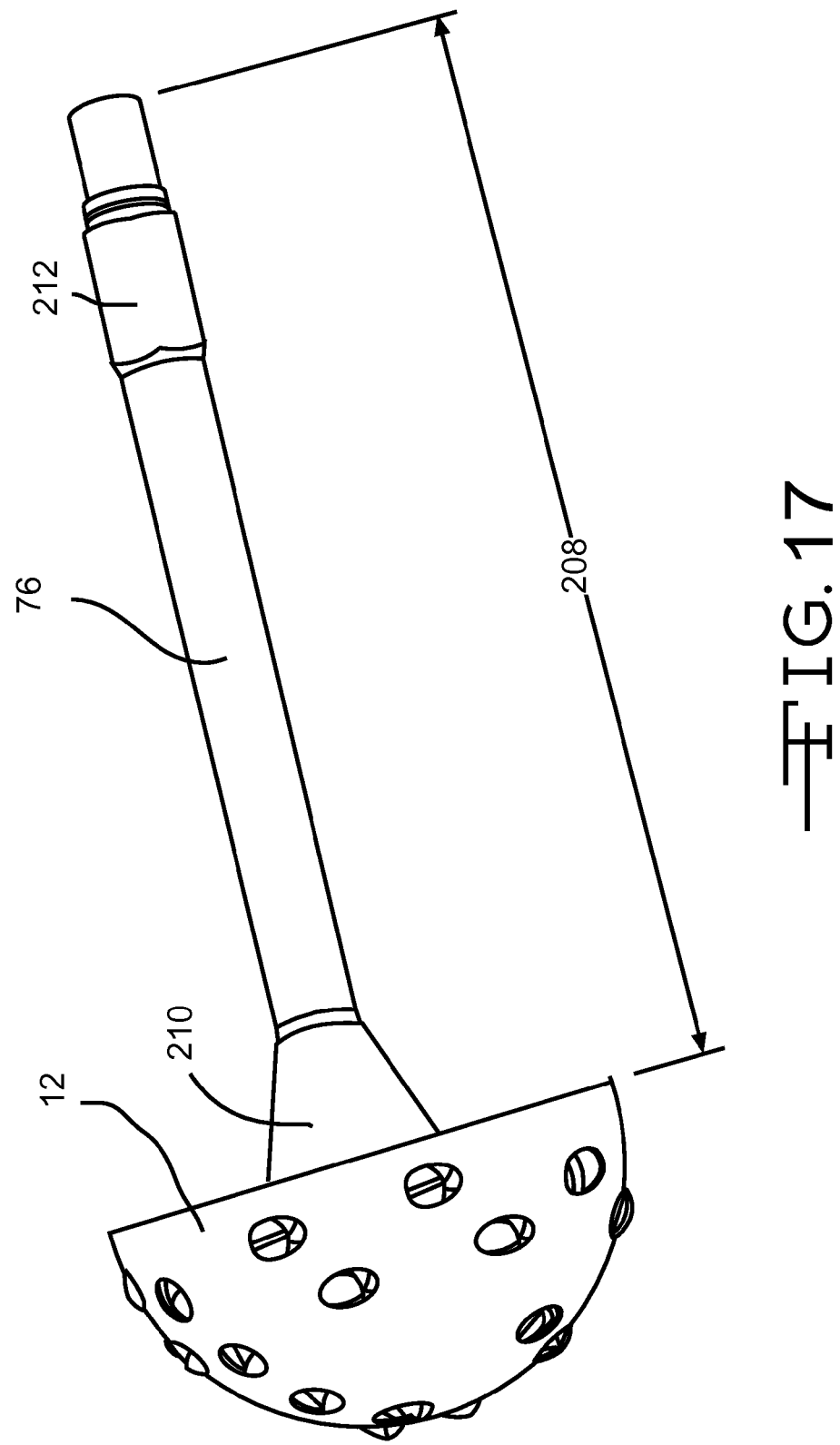
FIG. 17 shows an embodiment of a drive shaft connected to a cutting shell.

In addition to supporting the cutting shell 12, the frame 14 is designed to enable engagement of the bone cutter 10 with a drive shaft or spindle 76 (FIG. 17). FIGS. 1, 2 and 8 illustrate a preferred embodiment of the support frame 14 of the present invention comprising a cross-bar interface 88 that resides at the support frame base 70. The cross-bar interface 88 provides a means for connecting the reamer spindle 76 to the bone cutter 10. Thus, when the bone cutter 10 is connected to the spindle 76 a physician can operate the bone cutter 10 from a distal location. The bone cutter 10 can either be manually operated or, alternatively, be connected to a motor (not shown) to provide power assisted tissue removal. As shown, the frame cross-bar interface 88 comprises a first bar portion 90, a second bar portion 92, a third bar portion 94 and a fourth bar portion 96 that extend from respective support frame interior surfaces 54, 68 at the support frame base 70 and meet at the rotational axis C-C. It is noted that the cross-bar interface 88 may comprise more or less than four bar portions.

FIGS. 1-4 illustrate a preferred embodiment of the cutting shell 12 of the present invention. As previously mentioned, the cutting shell 12 comprises a plurality of spaced apart cutting teeth 26 that are positioned along the exterior surface 30 of the cutting shell 12. In a preferred embodiment, each of the cutting teeth 26 comprises an aperture 98 that extends through the cutting shell thickness. A cutting tooth raised portion 100 having a cutting surface 102 extends upwardly from the exterior shell surface 30. In a preferred embodiment, each cutting aperture 98 may be constructed having a shape that is similar to the letter "D" or "C". Each aperture 98 is dimensioned suitable for passing debris into an interior region of the support frame 14 where the debris may accumulate.

Furthermore, the tissue cutting surface 28 of the cutting teeth 26 at least partially extends about the perimeter of the aperture 98. More specifically, the tissue cutting surface 28 preferably resides above the cutting tooth aperture 98. Each of the raised portions 100 of the cutting teeth 26 is integrated with the body of the shell 12. In a preferred embodiment, the raised portion 100 comprises a first end 99 that extends to a second end 101 having the tissue cutting surface 28 therebetween. The first end is preferably an extension of the exterior shell surface and the tissue cutting surface 28 is an extension of the raised portion extending to the second end positioned spaced above the cutting tooth aperture 98. In other words, the raised structure 100 preferably comprises a partial hemispherical structure 103 having a partial dome base 105 that extends to a cutting dome apex 107 (FIG. 3) residing over the cutting tooth aperture 98. In preferred embodiment, the thickness of the cutting dome shell forms the thickness of the tissue cutting surface 28 of the tooth 26.

Figure 5:
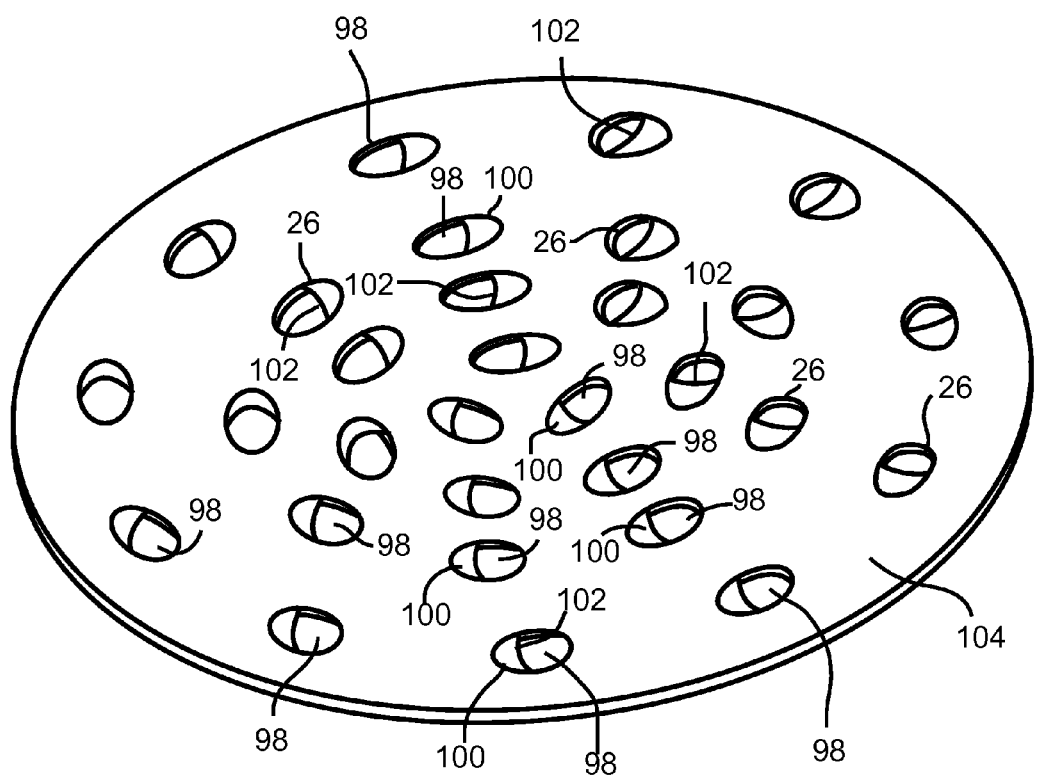
FIG. 5 illustrates an embodiment of a metal pre-form used to fabricate the cutting shell shown in FIG. 2.

In a preferred embodiment, the cutting shell 12 of the present invention is fabricated in a metal stamping process in which a sheet of flat stock metal is first cut out in the general shape of the bone cutter shell 12. FIG. 5 illustrates an embodiment of a sheet of flat stock metal that has been cut in a pre-form shape 104 of the cutter shell 12. Once the sheet of flat stock metal has been cut to the desired pre-form shape 104, the cutting teeth 26 are formed by a metal stamping process. In a preferred embodiment, the stamping process forms the cutting aperture 98 and bends a portion of the metal to form the raised portion 100 of the cutting tooth 26. In addition, the stamping process bends the pre-form shape 104 into the hemispherically shaped cutting shell 12.

Figure 6:
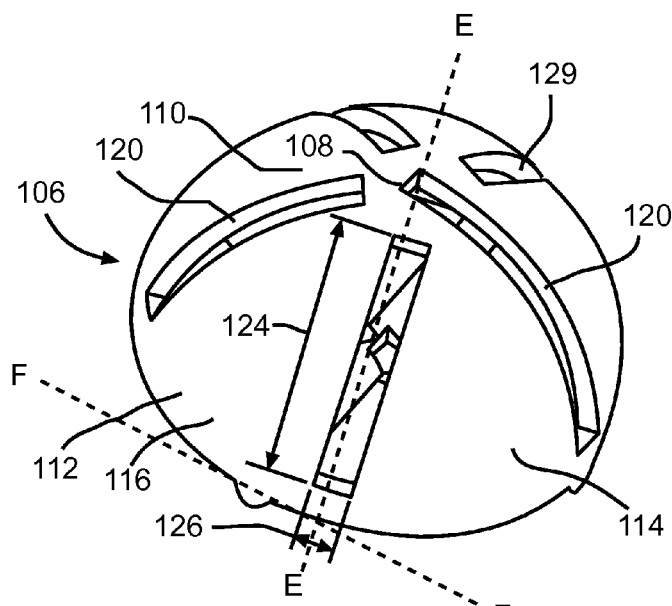
FIG. 6 illustrates an alternative embodiment of a support frame comprising a plurality of insert blade slots.
Figure 7:
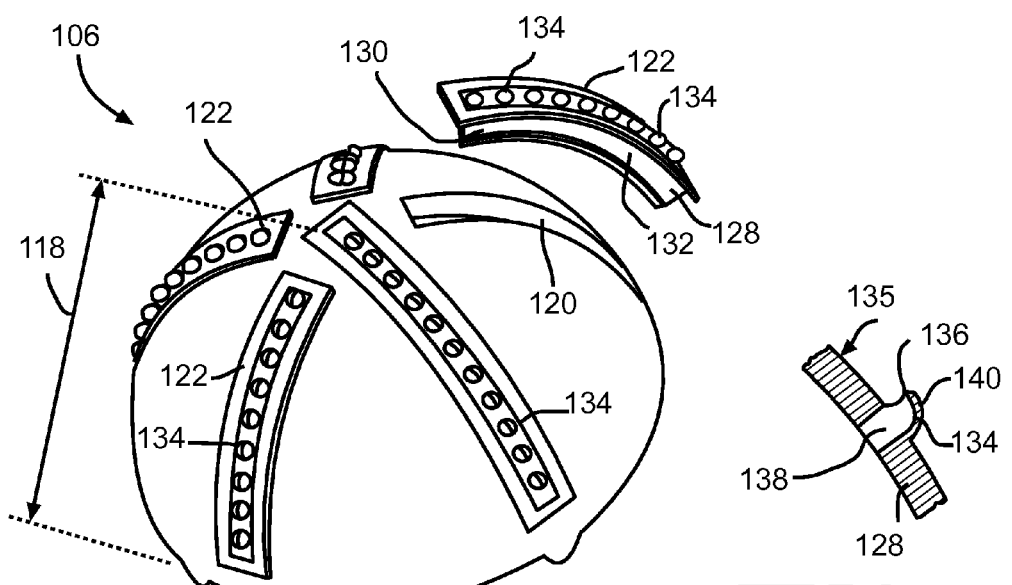
FIG. 7 shows an embodiment of a cutting shell with a plurality of cutting blade inserts positioned within the insert blade slots of the support frame shown in FIG. 6.
Figure 7A:
FIG. 7A is a magnified cross-sectional view of an insert blade cutting tooth.

FIGS. 6 and 7 illustrate alternate embodiments of a cutting shell 106 and support frame 105 thereof of the present invention. In this alternate bone cutter embodiment, a plurality of blade inserts 122 are removably positioned within respective blade insert slots 120 that extend through the thickness of an at least partially hemispherical shaped support frame 105. Thus, by inserting the plurality of blade inserts 122 within their respective blade insert slots 122, the support frame 105 becomes a cutting shell 106 that may be used during a surgical procedure.

As shown in FIG. 6, the support frame 105 is generally of a domed shape having at least a partially hemispherical shape. As illustrated, the support frame 105 comprises a shell apex 108 located at a support frame distal end 110 that extends to a shell base 112 located at an imaginary equatorial base plane F-F (FIG. 6) at a shell proximal end 114. A rotational axis E-E extends through the apex 108.

The support frame shell base 112 defines an annular support frame outer perimeter at a lower base edge 116 of the shell 106 having a diameter ranging from about 20 mm to about 80 mm. The support frame shell 105 also has a height 118 that extends from the lower base edge 116 to the apex 108 (FIG. 7). It is preferred that the support frame shell height 118 may range from about 10 mm to about 50 mm.

In addition, the support frame 105 may also comprise a cross-bar interface 88, as previously described, to provide a means for connecting the reamer spindle 76 (FIG. 17) to the cutting shell 106. In this embodiment, the cross-bar interface 88 is positioned at the support frame shell base 112.

The support frame shell 105 further comprises a plurality of slots 120 that extend through the thickness of the support shell 105. These slots 120 provide a means for receiving the cutting blade insert 122 therewithin. In a preferred embodiment, the plurality of cutting blade insert slots 120 is oriented longitudinally along the shell 105. Each of the slots 120 comprises a length 124 and a width 126 that are dimensioned to receive the insert 122. In a preferred embodiment, the slots 120 are positioned such that their lengths 124 extend longitudinally along the hemispherically curved surface of the shell 105. As illustrated in FIG. 6, in a preferred embodiment, at least a portion of one of a slot 120 extends through the rotational axis E-E at the shell apex 108. This helps ensure a thorough cut when a respective blade insert 122 is positioned therewithin. In addition, it is preferred that the slots 120 are positioned in a staggered orientation from each other to increase the total surface area of the bone or tissue that is cut to thus create a cavity having a smooth semi hemispherical surface.

Each blade insert 122 comprises an insert body 128 that is dimensioned to be removably positioned within respective blade insert slots 120. In a preferred embodiment, the blade insert 122 may comprise a flange 130 that outwardly extends from an external sidewall surface 132 of the insert body 128. This flange 130 helps to engage the blade insert 122 within the respective blade insert slot 120 such that a snug interference fit is established therewithin.

In a preferred embodiment, each of the blade inserts 122 comprises a series of spaced apart cutting teeth 134 positioned within the insert 122. More specifically, each of the insert cutting teeth 134 comprises a tissue cutting surface 136 that at least partially extends above a top surface 135 of the insert body 128. In addition, the tissue cutting surface 136 preferably extends about a perimeter of a cutting tooth aperture 138 that extends at least partially within a depth of the insert body 128. As illustrated, the tissue cutting surface 136 preferably resides above the cutting tooth aperture 138. Each of the plurality of cutting teeth 134 comprises a raised portion 140 that is integrated with the body 128 of the insert 122. In a preferred embodiment, the raised portion 140 comprises a first end that extends to a second end having the tissue cutting surface 136 therebetween.

FIG. 8 illustrates an alternative embodiment of a cutting shell 142 that may be used with the support frame 14 of the present invention. As shown, the cutting shell 142 comprises a plurality of spaced apart longitudinally extending first ribs 144 and laterally extending second ribs 146 that together form at least a partial hemispherical shape. More specifically, the plurality of first ribs 144 extend longitudinally along rotational axis G-G from a first rib distal end 148 positioned at a shell apex 150 to a first rib proximal end 152 residing at a shell base 154. The plurality of spaced apart second ribs 146 extend laterally between adjacent longitudinally positioned first ribs 144 from a second rib distal end 156 to a second rib proximal end 158. Alternatively, the plurality of second ribs 146 may be positioned along an interior surface 160 of the first ribs 144. The resulting shell structure 142 thus comprises a series of windows 162 that are formed by the intersection of the longitudinal and laterally positioned first and second ribs 144, 146. These windows 162 preferably provide a means for tissue and bone debris to exit the bone cutter 10. Furthermore, the plurality of windows 162 provide a means for positioning a frame attachment mechanism therethrough. For example, a fastener such as a rivet or screw may be positioned through a window 162 to thereby attach the shell 142 to the frame 14.

Figure 8A:
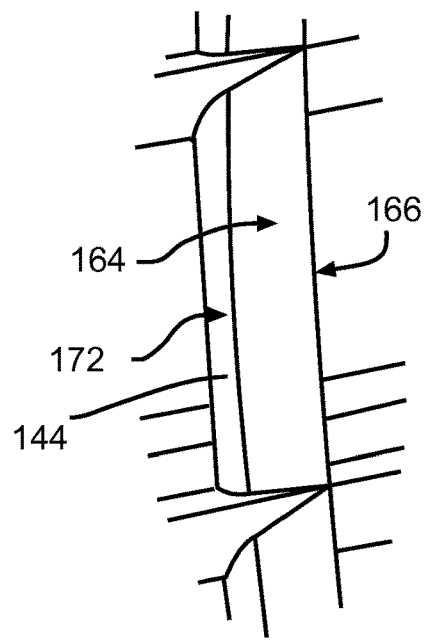
FIG. 8A is a magnified view illustrating the cutting surface that extends from the exterior rib surface of the cutting shell shown in FIG. 8.

FIG. 8A illustrates a magnified view of a portion of an exterior shell surface 164 of a first rib 144 shown in FIG. 8. In a preferred embodiment, the exterior surface 164 of the first rib 144 is constructed at an offset angle relative to rotational axis G-G. More specifically, the first rib exterior surface 164 forms the cutting blade of the cutting shell 142. As illustrated, a tissue cutting surface 166 is formed at the distal end of the exterior first rib surface 164. As shown, the tissue cutting surface 166 extends at an angular direction relative to the rotational axis G-G from first rib sidewall surface 172. In a preferred embodiment, the tissue cutting surface 166 extends toward the direction of cut as the cutting shell 142 is rotated about its rotational axis G-G.

Figure 9A:
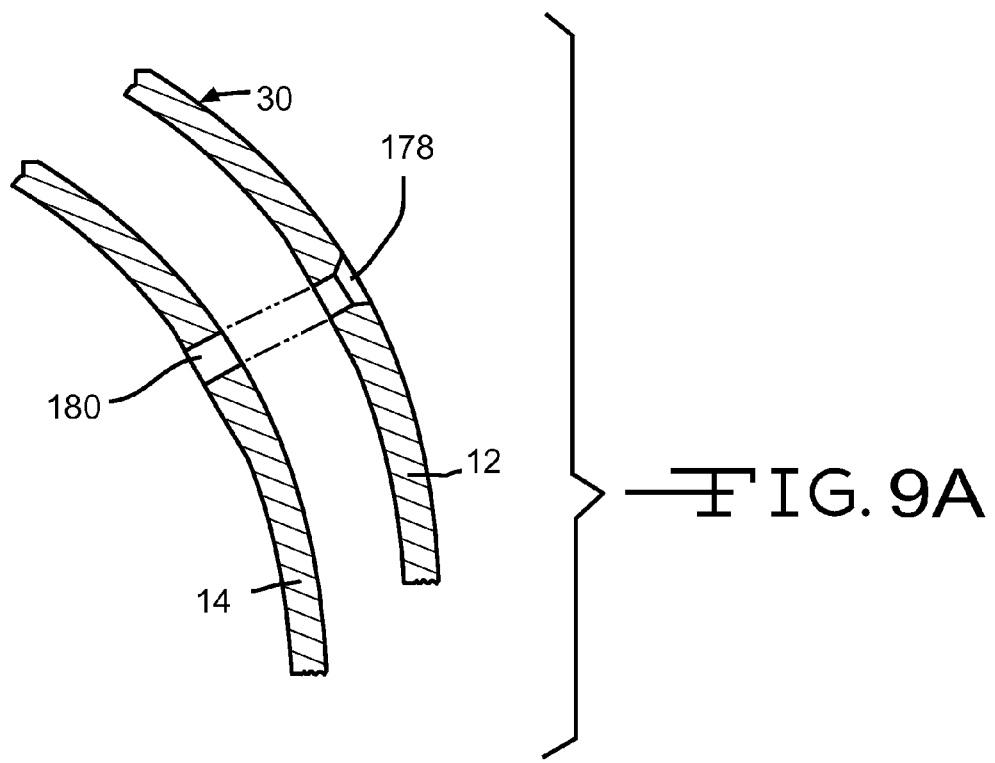
FIGS. 9A and 9B is a magnified cross-sectional view that illustrates an embodiment of a support frame and cutting shell attachment mechanism in which a fastener extends through first and second through holes that respectively extend through the cutting shell and support frame sidewall thicknesses.
Figure 9B:
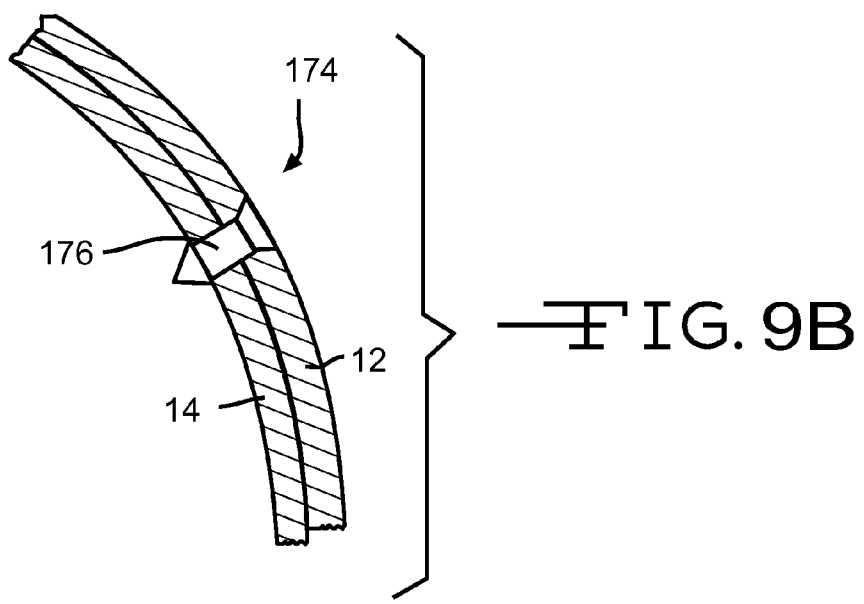

A plurality of attachment mechanisms may be used to removably connect the support frame 14 to the variety of different cutting shells 12, 106, 142 disclosed in the present application. The following examples of attachment mechanisms represent a plurality of non-limiting mechanisms that may be used to connect the frame 14 to the shell 12, 105, 142. FIGS. 9A and 9B illustrate an embodiment of a frame and cutting shell fastener attachment mechanism 174. In this example, at least one fastener 176, such as a rivet or screw, is positioned through a first through-bore 178 that extends through the thickness of the cutting shell sidewall and a second through-bore 180 that extends through a thickness of the frame 14, thereby connecting them together (FIG. 9B). In a preferred embodiment, at least one first through-bore 178 having a beveled opening at the shell exterior surface 30 extends through the cutting shell thickness at the cutting shell base. This preferred location thus minimizes potential interferences of the fastener with the tissue and bone intended to be cut. In addition, the end of the fastener is preferably about flush with the cutting shell exterior surface 30. This also ensures that the end of the fastener 176 does not interfere with the cutting surface 28 of the cutting shell 12. Furthermore, it is preferred that the fastener is composed of a material such as a polymer so that it can be snapped or cut to thereby remove the cutting shell 12 from the frame 14. Other examples of fasteners, may include, but are not limited to, a screw, a bolt or an anchor molly.

Figure 10:
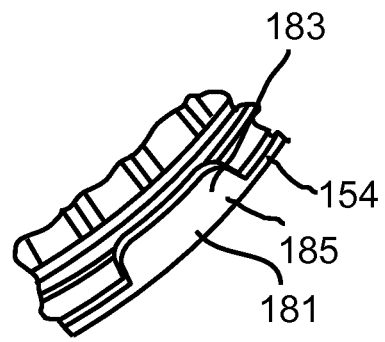
FIG. 10 shows an embodiment of an attachment mechanism comprising a plurality of tabs that are positioned at the base of a cutting shell.

FIG. 10 illustrates an additional attachment embodiment of the present invention. In this embodiment a plurality of tab portions 181 are positioned at the base of the cutting shell 12. In a preferred embodiment, each of the tab portions 181 extends inwardly towards the shell rotational axis from the cutting shell base perimeter. As shown, a tab distal portion 183 extends towards the rotational axis from a tab proximal portion 185 that is positioned along the base edge of the cutting shell. The tab portions 181 are designed such that they enable the support frame 14 to snap into position within the interior 16 of the cutting shell 12, 106, 142. In a preferred embodiment, as the support frame 14 is positioned within the interior 16 of the shell 12, the plurality of tab portions 181 flex inwardly towards the rotational axis, thereby allowing the support frame 14 to be positioned within the interior of the cutting shell. Once the support frame 14 is positioned within the shell, the tab portions 181 snap back into their original positions, thus holding the frame therewithin. The support frame 14 may be removed by breaking the tab portions 181.

In a preferred embodiment, the tab 181 may engage with the ledge 78 that extends at the base of the support frame 14 as previously discussed and illustrated in FIG. 2A. In this embodiment, the tab 181 may comprise a through-bore that extends through the tab thickness. The ledge lip 86 may be positioned within the tab through-bore to connect the frame 14 with the cutting shell. In this embodiment, the lip 86 maybe of a greater diameter than the throughbore that extends through the thickness of the tab 181, thereby creating an interference fit therebetween.

Figure 11:
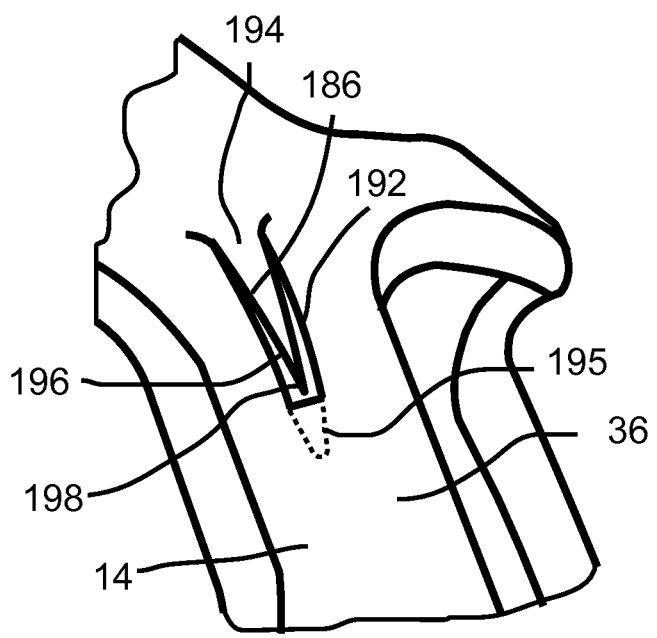
FIG. 11 shows an embodiment of a groove partially positioned within the support frame sidewall that may be used in a tongue and groove attachment mechanism.
Figure 12A:
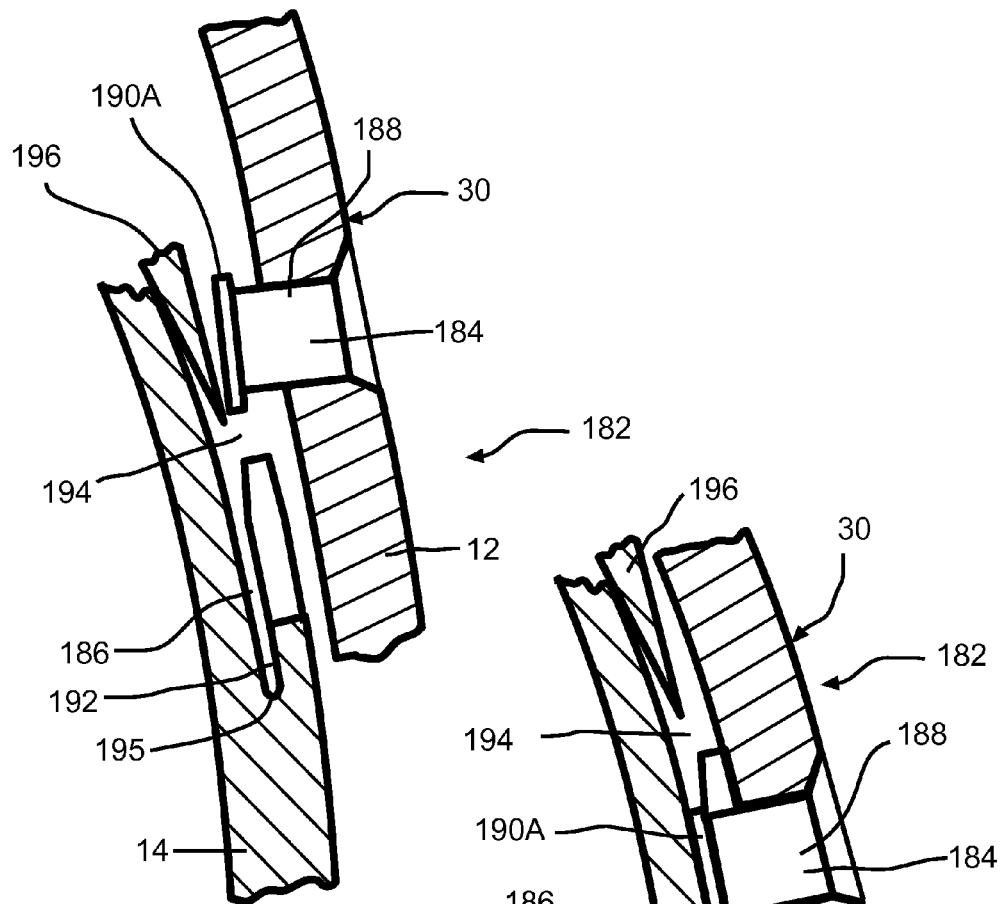
FIGS. 12A and 12B illustrate an embodiment of a tongue and groove attachment mechanism that may be utilized to removably connect the support frame to a cutting shell.
Figure 12B:
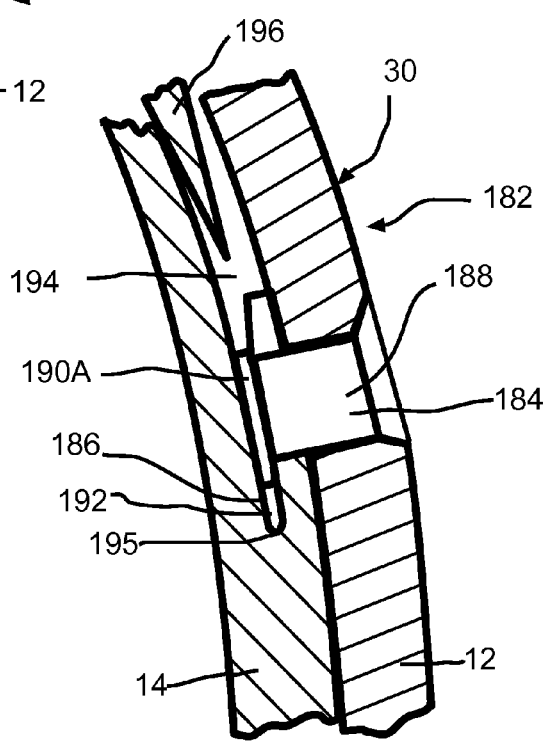

FIGS. 11, 12A and 12B illustrate an embodiment of a tongue and groove attachment mechanism 182 that may be used with the bone cutter 10 of the present invention. In this example, a tongue member 184 is removably received within a groove 186 that at least partially resides within the exterior surface 56, 66 of the support frame 14 (FIG. 11). This ensures a secure connection between the cutting shell 12, 106, 142 and support frame 14 during a surgical procedure while also allowing for the support frame 14 to be easily removed.

FIG. 11 illustrates an embodiment of the groove 186 that may be used to receive the tongue member 184 of the attachment mechanism. As shown, the groove 186 preferably comprises a groove track 192 that extends from a distal groove location 194 to a proximal groove location 195 that resides at least partially within the exterior surface of the support frame 14. In a preferred embodiment, the groove 186 may be constructed such that the width of the groove track 192 progressively narrows from the groove track distal end 194 to the groove track proximal end 195. This tapered groove track design 192 securely captures the post 188 and engagement end 190 therewithin, thereby minimizing displacement of the shell 12, 106, 142 with respect to the support frame 14, particularly during an orthopedic procedure. The tapered width of the groove track 192 helps secure the post 188 and engagement end 190 therewithin when the shell 12 is related relative to the frame 14. More specifically, the engagement end 190 is slid into the groove 186 as the frame 14 is slid in a distal direction towards the shell apex 18.

In addition, the groove 186 may also comprise a tab portion 196 that at least partially extends from either or both of the opposing sidewalls of the groove track 192. In a preferred embodiment, the tab 196 extends from a position that is proximate the exterior surface 56, 68 of the support frame 14 along the interior of the opposing grove track sidewalls. In addition, the tab 196 may comprise a slit 198 that at least partially extends in a proximal direction from the proximal tab end. The tab 196 helps capture the post 188 and engagement end 190 within the groove track 192.

FIGS. 12A and 12B illustrate a preferred embodiment in which the post engagement end 190 is received within the frame sidewall groove 186 as the frame 14 is positioned within the interior of the cutting shell 12. As shown in FIG. 12A, the engagement end 190A is initially received within the grove 186. An axial force along axis B-B is applied to the base of the frame 14 in a distal direction to securely position the frame 14 therewithin. As illustrated in FIG. 12B, as the frame 14 is moved into position, the engagement end 190 is removably locked into position within the groove track 192. The tab 196 extends outwardly and serves to at least partially cover the proximal opening of the groove 186 to help ensure debris does not enter the groove track 192. To remove the frame 14, a force is applied in an opposite proximal direction along axis B-B against the frame 14 to thereby disengage the frame 14 from the cutting shell 12.

Figure 13A:
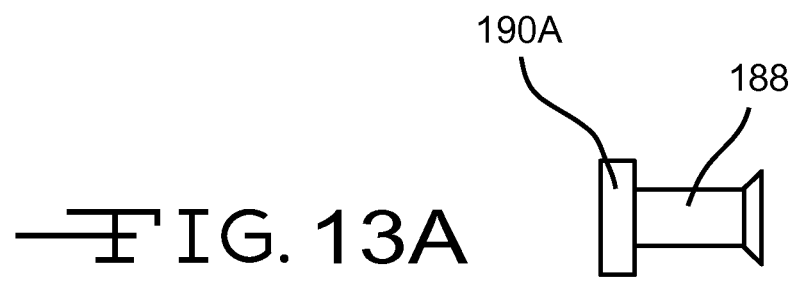
FIGS. 13A-13C illustrate various embodiments of different tongue members.
Figure 13B:
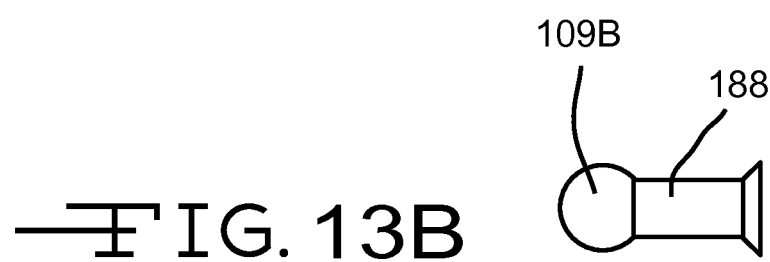
Figure 13C:

In a preferred embodiment, the post engagement end 190 may comprise a plurality of shapes and sizes such that they are removably receivable within the groove 186. FIGS. 13A-13C illustrate a plurality of tongue members 186 comprising a variety of non-limiting engagement portion embodiments. Examples of which may include but are not limited to a plate 190A, a ball 190B, or a series of sprockets 190C that radially extend outward from the post 188.

Figure 14:
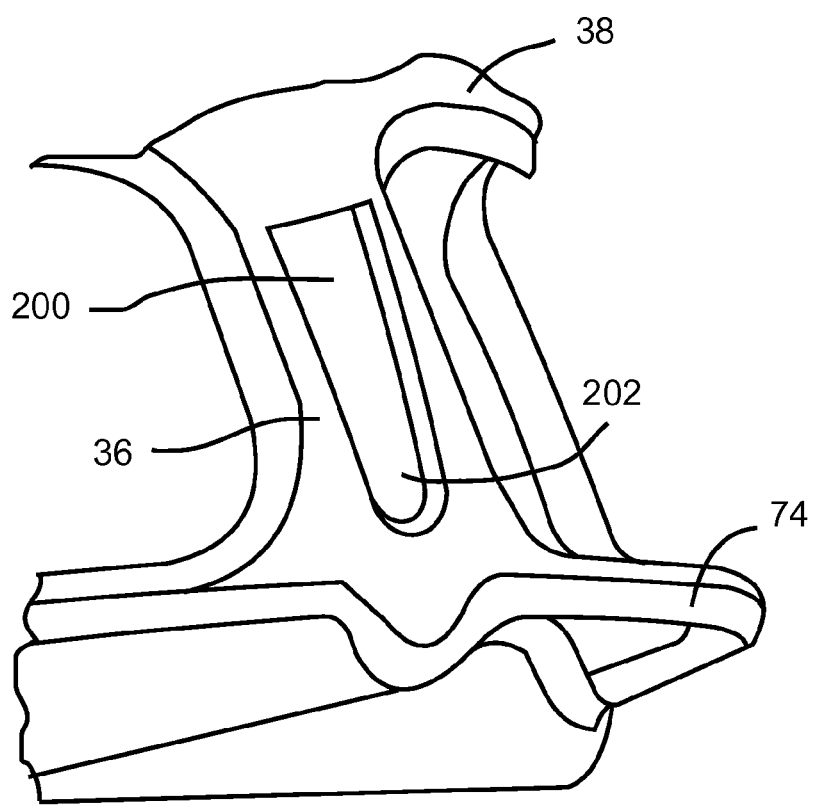
FIG. 14 illustrates an embodiment of an opening that extends through a sidewall thickness of the support frame in which various tongue members may extend therethrough securing the support frame to the cutting shell.

Alternatively, as illustrated in FIG. 14, the post 188 and engagement portion 190 may be received through a slot 200 that extends through the thickness of the frame sidewall. As shown, the slot 200 comprises an opening having a chevron shape oriented perpendicular to the sidewall thickness. A narrowed "V" shaped portion 202 of the chevron shaped opening extends proximally towards the support frame base 22. This preferred chevron shape enables the post and engagement portion 188, 190 thereof to securely wedge within the narrowed "V" portion 202 of the opening when the post 188 is aligned with the slot 200 and then with continued relative axial movement along axis B-B.

FIG. 15 illustrates a non-limiting embodiment in which a series of posts 188 may extend from an interior surface of the cutting shell 12, 106, 142. In this attachment embodiment, at least one post 188 preferably may engage with the support frame groove 186 or, alternatively, the post 188 may engage through support frame slot 200. It is further contemplated that the posts 188 shown extending from the interior surface of the cutting shell 12, 106, 142, may also comprise an engagement portion that is received within the support frame 14. As before, the shell 12 is locked to the frame 14 when the post 188 is aligned with the groove 186 or slot 200 and then with continued relative axial movement along axis B-B.

Figure 16A:
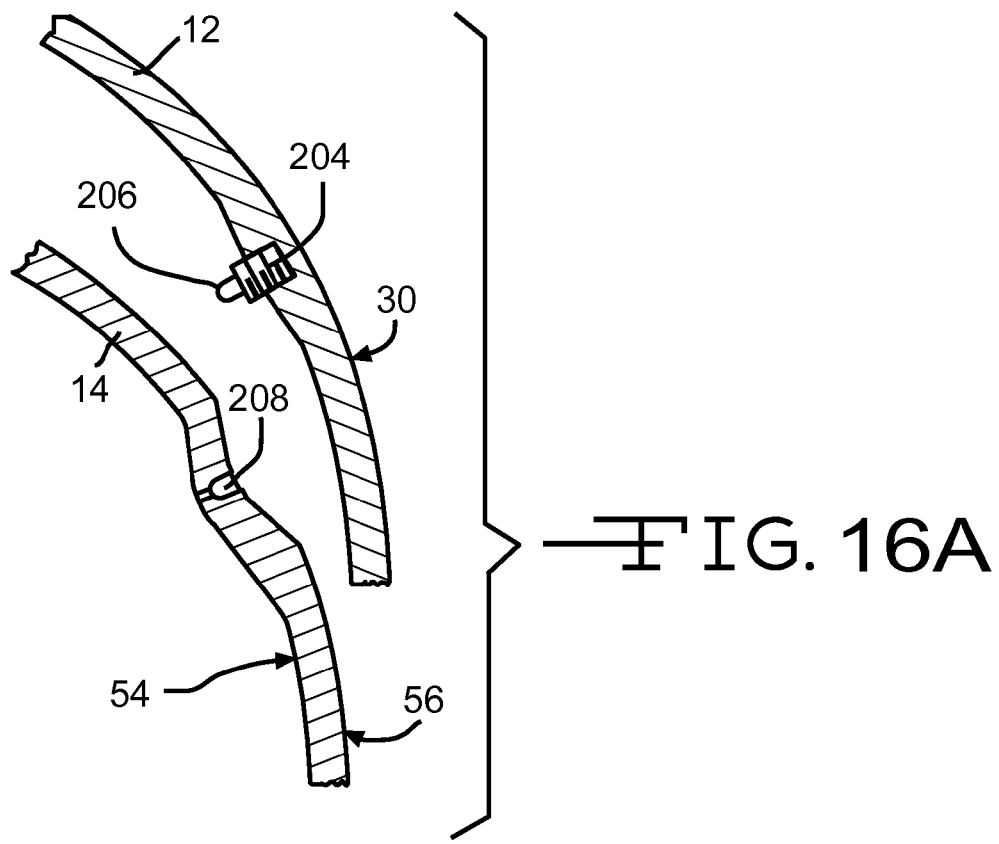
FIGS. 16A and 16B illustrate an alternate embodiment of an attachment mechanism in which a bias catch pin extends from an interior surface of a cutting shell that removably engages with the support frame.
Figure 16B:
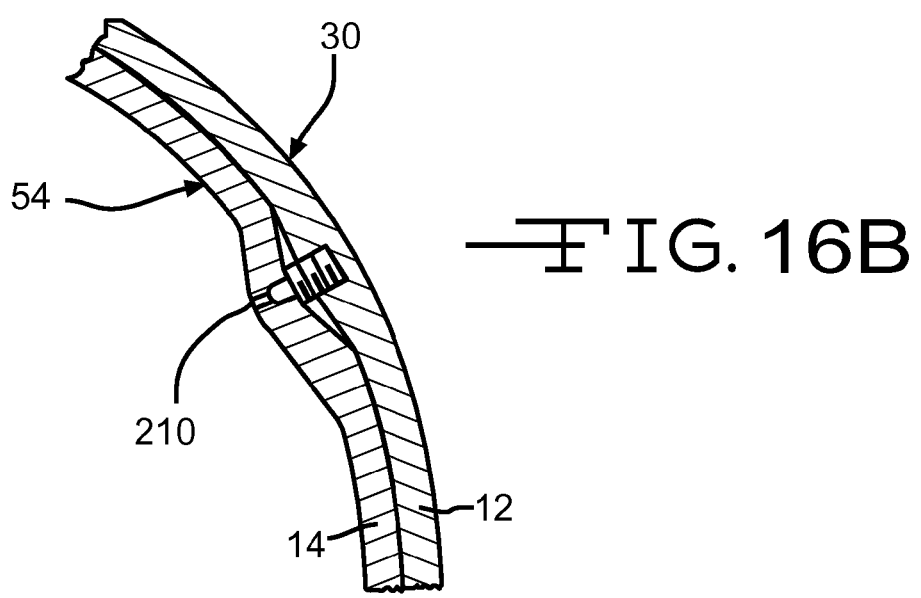

FIGS. 16A and 16B illustrate yet another embodiment of a catch pin attachment mechanism. In this embodiment, a catch pin housing 204 positioned within the thickness of the cutting shell may be used to secure the support frame 14 thereto. In a preferred embodiment, the catch pin housing 204 comprises a pin 206 which at least partially extends from the housing. The pin 206 is capable of a sliding motion such that the pin may extend in and out of the housing. A bias member (not shown) resides within the housing and is positioned in back of the pin 206. The bias member provides a force that extends the pin 206 out of the housing 204. A pin receiving hole 208 is preferably positioned within the thickness of the support frame 14 sidewall. The receiving hole is designed to receive and capture the pin 206 when positioned therewithin. In a preferred embodiment, the bias force extends the pin 206 within the pin receiving hole 208 when the pin 206 and the receiving hole 208 are aligned. The pin 206 snaps into the receiving hole 208 and is secured therein. For example, the pin 206 may be designed having a diameter that is slightly greater than the diameter of the receiving hole 208 thereby the pin 206 creates an interference fit therewithin. In addition, the receiving hole 208 may comprise an annular ridge that extends from an interior receiving hole surface. Thus, the pin 206 may be positioned such that is extends past the extending annular ridge securing it into place.

The catch pin can be disengaged from the support frame 14 by extending a release pin (not shown) through a catch pin pilot hole 210 that extends through the thickness of the support frame 14. In a preferred embodiment, the release pin acts on the distal end of the pin 206 that forces pin 206 to retract within the catch pin housing. When the pin 206 is retracted within the housing, the support frame 14 can be removed from the cutting shell 12, 106, 142.

FIG. 17 illustrates an embodiment of a drive shaft or spindle 76 that may be used to control and maneuver the bone cutter 10. As shown, the drive shaft 76 comprises a drive shaft length 208 extending from a drive shaft proximal end 210 to a drive shaft distal end 212. In a preferred embodiment, the bone cutter 10 may be detachably fastened to the drive shaft distal end 212 and the drive shaft proximal end 210 may be used as a handle or, alternatively, may be connected to a motorized mechanism (not shown). In a preferred embodiment, the base of the frame 22 may be detachably fastened to the drive shaft distal end 212.

While the preferred embodiments of the cutting device and methods have been described in reference to the environment in which they were developed, they are merely illustrative of the principles of the inventions. Other embodiments and configurations may be devised without departing from the spirit of the inventions and the scope of the appended claims.

What is claimed is:

1. A bone cutter, comprising:
   a) a support frame, comprising:
      i) a frame base residing along an imaginary base plane;
      ii) a plurality of first struts, each first strut extending from a first strut proximal end connected to the frame base to a first strut distal end spaced from an imaginary apex of the support frame, wherein a rotational axis extends perpendicular to the imaginary base plane and through the imaginary apex;
      iii) a plurality of second struts, each second strut extending laterally to adjacent ones of the first struts; and
      iv) a cross-bar connected to the frame base, the cross-bar being detachably connectable to a drive shaft;
   b) a semi-hemispherical, hollow cutting shell extending from an equatorial rim to a cutting shell apex, wherein a central rotational axis of the cutting shell is aligned with the cutting shell apex, but spaced from the equatorial rim; and
   c) a plurality of cutting teeth arrayed along the cutting shell,
   d) wherein the support frame is removably positionable within an interior of the cutting shell such that rotational movement of the support frame connected to the cutting shell causes rotation about the rotational axis of the support frame and central rotational axis of the cutting shell.

2. The bone cutter of claim 1, wherein a cutting surface of each of the cutting teeth extends at least partially over an aperture extending through the cutting shell.

3. The bone cutter of claim 1, wherein each of the first struts curve in a partially hemispherical shape from the first strut proximal end connected to the frame base to the first strut distal end spaced from the imaginary apex of the support frame.

4. The bone cutter of claim 1, wherein at least one first through bore extends through the cutting shell and at least one second through bore extends through at least one of the plurality of first and second struts of the support frame, and wherein at least one fastener is positioned within correspondingly located first and second through bores to connect the cutting shell to the support fame.

5. The bone cutter of claim 4, wherein the fastener is selected from the group consisting of a rivet, a screw, a bolt, and a sprocket.

6. The bone cutter of claim 1, wherein a post having an engagement end extends from an interior surface of the cutting shell, and wherein a groove is provided within an exterior surface of one of the first and second struts, the engagement end of the post being engagable with the groove to thereby connect the cutting shell to the support frame.

7. The bone cutter of claim 6, wherein the engagement end of the post has a shape selected from the group consisting of a plate, a ball and a sprocket.

8. The bone cutter of claim 1, wherein the support frame is composed of a polymeric material, a metal, a ceramic material, or combinations thereof.

9. The bone cutter of claim 1, wherein the frame base provides a ledge, and wherein the cutting shell is at least partially supported on the ledge.

10. A bone cutter, comprising:
    a) a support frame, comprising:
       i) a plurality of vertical struts extending from a vertical strut proximal end to a vertical strut distal end, wherein the vertical strut distal ends are spaced proximally from an imaginary apex of the support frame;
       ii) a plurality of first horizontal struts, each first horizontal strut residing on an imaginary equatorial plane and extending laterally between adjacent ones of the vertical struts;
       iii) a plurality of second horizontal struts, each second horizontal strut extending laterally between adjacent ones of the vertical struts, wherein the second horizontal struts are spaced closer to the imaginary apex of the support frame than the first horizontal struts; and
       iv) a cross-bar connected to the plurality of vertical struts, the cross-bar being detachably connectable to a drive shaft; and
    b) a semi-hemispherical, hollow cutting shell extending from a cutting shell equatorial rim to a cutting shell apex, wherein a first rotational axis central to the cutting shell is aligned with the cutting shell apex, but spaced from the equatorial rim; and
    c) a plurality of cutting teeth arrayed along the cutting shell,
    d) wherein the support frame is removably positionable within an interior of the cutting shell such that rotational movement of the support frame connected to the cutting shell causes rotation about the first rotational axis.

11. The bone cutter of claim 10, wherein the first horizontal struts of the support frame provide a ledge, and wherein the cutting shell is at least partially supported on the ledge.

12. The bone cutter of claim 10, wherein a second rotational axis extends perpendicular to the support frame imaginary equatorial plane and through the support frame imaginary apex.

13. The bone cutter of claim 12, wherein both an exterior surface of the plurality of vertical struts and an exterior surface of the plurality of first and second horizontal struts have a convex shape with respect to the second rotational axis.

14. The bone cutter of claim 12, wherein there are four vertical struts curving to respective vertical strut distal ends spaced from the imaginary apex of the support frame.

15. The bone cutter of claim 14, wherein the four vertical struts are equally spaced about a perimeter of the support frame.

16. The bone cutter of claim 15, wherein there are four first horizontal struts and four second horizontal struts, and wherein the first and second horizontal struts extend laterally between adjacent ones of the four vertical struts.

17. The bone cutter of claim 15, wherein the cross-bar has spaced apart ends secured to opposed pairs of the four vertical struts, the cross-bar extending perpendicular to the second rotational axis of the support frame and being configured for detachable connection to the drive shaft.

18. The bone cutter of claim 10, wherein a cutting surface of each of the plurality of cutting teeth extends at least partially over an aperture extending through the cutting shell.

19. The bone cutter of claim 10, wherein at least one first through bore extends through the cutting shell and at least one second through bore extends through at least one of the plurality of vertical struts and the first and second horizontal struts of the support frame, and wherein at least one fastener is positioned within correspondingly located first and second through bores to connect the cutting shell to the support fame.

20. The bone cutter of claim 19, wherein the fastener is selected from the group consisting of a rivet, a screw, a bolt, and a sprocket.

21. The bone cutter of claim 10, wherein at least one post extends from an interior surface of the cutting shell, and wherein at least one of the plurality of vertical struts and first and second horizontal struts of the support frame is provided with a groove, and wherein the post is receivable within the correspondingly located groove to thereby connect the cutting shell to the support frame.

22. The bone cutter of claim 10, wherein the support frame is composed of a polymeric material, a metal, a ceramic material, or combinations thereof.

23. A bone cutter, comprising:
   a) a support frame, comprising:
      i) four vertical struts, each vertical strut curving from a vertical strut proximal end to a vertical strut distal end, wherein the vertical strut distal ends are spaced proximally from an imaginary apex of the support frame;
      ii) four first horizontal struts, each first horizontal strut residing on an imaginary equatorial plane and extending laterally between adjacent ones of the vertical struts; and
      iii) four second horizontal struts, each second horizontal strut extending laterally between adjacent ones of the vertical struts, wherein the second horizontal struts are spaced closer to the imaginary apex of the support frame than the first horizontal struts; and
      iv) a cross-bar connected to the four vertical struts, the cross-bar being detachably connectable to a drive shaft,
      v) wherein a first rotational axis extends perpendicular to the support frame imaginary equatorial plane and through the support frame imaginary apex; and
   b) a semi-hemispherical, hollow cutting shell extending from a cutting shell equatorial rim to a cutting shell apex, wherein a second rotational axis central to the cutting shell is aligned with the cutting shell apex, but spaced from the equatorial rim; and
   c) a plurality of cutting teeth arrayed along the cutting shell,
   d) wherein the support frame is removably positionable within an interior of the cutting shell for rotational movement of the support frame connected to the cutting shell about the respective first and second co-axially aligned rotational axes.

24. The bone cutter of claim 23, wherein the cross-bar has spaced apart ends secured to opposed pairs of the four vertical struts, the cross-bar extending perpendicular to the first rotational axis of the support frame and being configured for detachable connection to the drive shaft.

25. The bone cutter of claim 24, wherein at least one first through bore extends through the cutting shell and at least one second through bore extends through at least one of the plurality of vertical struts and the first and second horizontal struts of the support frame, and wherein at least one fastener is positioned within correspondingly located first and second through bores to connect the cutting shell to the support fame.

26. The bone cutter of claim 24, wherein at least one post extends from an interior surface of the cutting shell, and wherein at least one of the plurality of vertical struts and first and second horizontal struts of the support frame is provided with a groove, and wherein the post is receivable within the correspondingly located groove to thereby connect the cutting shell to the support frame.

27. The bone cutter of claim 23, wherein the first horizontal struts of the support frame provide a ledge, and wherein the cutting shell is at least partially supported on the ledge.

28. The bone cutter of claim 23, wherein the first and second horizontal struts are curved so that along with the curved vertical struts, the support frame has a partial semi-hemispherical shape.

* * * * *